United States Patent [19]

Digenis et al.

[11] Patent Number: 5,162,307
[45] Date of Patent: Nov. 10, 1992

[54] POLYMER BOUND ELASTASE INHIBITORS

[75] Inventors: George A. Digenis, Lexington, Ky.; Bushra J. Agha, Nanuet, N.Y.; William R. Banks, Louisville, Ky.; Frantisek Rypacke, Prague, Czechoslovakia

[73] Assignees: Board of Trustees of the University of Kentucky, Lexington, Ky.; Czechoslovak Academy of Sciences, Czechoslovakia

[21] Appl. No.: 857,119

[22] Filed: Mar. 25, 1992

Related U.S. Application Data

[63] Continuation of Ser. No. 242,294, Sep. 9, 1988, abandoned.

[51] Int. Cl.$^5$ ............... A61K 37/00; A61K 37/02; C07K 5/00; C07K 7/00
[52] U.S. Cl. ................................ 514/19; 514/18; 530/331; 530/323; 525/54.1
[58] Field of Search ............... 514/18, 19; 530/331, 530/397; 435/179; 525/54.1

[56] References Cited

U.S. PATENT DOCUMENTS

| | | | |
|---|---|---|---|
| 3,853,708 | 12/1974 | Porath et al. | 435/179 |
| 3,960,666 | 6/1976 | Bourdeau et al. | 435/179 |
| 4,013,514 | 3/1977 | Wildi et al. | 435/99 |
| 4,033,817 | 7/1977 | Gregor | 435/44 |
| 4,433,054 | 2/1984 | Chibata et al. | 435/178 |
| 4,496,689 | 1/1985 | Mitra | 525/54.1 |

OTHER PUBLICATIONS

Tuhy, Peter M. and Powers, James C.: "Inhibition of Human Leukocyte Elastase by Peptide Chloromethyl Ketones", Feb. 1975.
Powers, James C., Gupton, B. Frank, Harley, A. Dale, Nishino, Norikazu and Whitley, Ronald J.: "Specificity of Porcine Pancreatic Elastase, Human Leukocyte Elastase and Cathepsin G, Inhibition with Peptide Chloromethyl Ketones", Biochemica et Biopysica Act. 485 (1977) 156-166.
Yoshimura, Toshiaki, Barker, Larry N. and Powers, James C.: "Specificity and Reactivity of Human Leukocyte Elastase, Porcine Pancreatic Elastase, Human Granulocyte Cathepsin G. and Bovine Pancreatic Chymotrypsin with Arylsulfonyl Fluorides" J. Biol. Chem. 257, 5077-5084 (1972).
Groutas, William C., Abrams, William R., Theodorakis, Michael C., Kasper, Annette M., Rude, Steven A. Badger, Robert C., Ocain, Timothy D., Miller, Kevin E., Moi, Min K., Brubaker, Michael J., Davis, Kathy S. and Zandler, Melvin E.: "Amino Acid Derived Latent Isocyanates: Irreversible Inactivation of Porcine Pancreatic Elastase and Human Leukocyte Elastase", J. Med. Chem. 1985 28, 204-209.
Digenis, George A., Agha, Bushra J., Tsuji, Kiyoshi, Kato, Masayuki and Shinogi, Masaki; "Peptidyl Carbamates Incorporating Amino Acid Isosteres as Novel Elastase Inhibitors" Journal of Medicinal Chemistry, 1986, 29, 1468.
Zimmerman, Morris, Morman, Harriet, Mulvey Dennis, Jones, Howard, Frankshun, Robert and Ashe, Bonnie M.; "Inhibition of Elastase and Other Serine Proteases by Heterocyclic Acylating Agents", Journal Biol. Chemistry, vol. 255, No. 20 pp. 9848-9851 1980.
Janoff, Aaron and Dearing, Rosemarie: "Prevention of Elastase-Induced Experimental Emphysema by Oral Administration of a Synthetic Elastase Inhibitor", American Review of Respiratory Disease, vol. 121, 1980.
Tsuji, K., Agha, B. J., Shinogi, M. and Digenis, G. A.: "Peptidyl Carbamate Esters: A New Class of Specific Elastase Inhibitors", Biochem. & Biophys. Comm. vol. 122, No. 2, 1984 pp. 571-576.
Scofield, Rolfe E., Werner, Robert P. and Wold, Finn: "p-Nitrophenyl Carbamates as Active-Site-Specific Reagents for Serine Proteases", Biochemistry 16 (11) (1977).
Ashe, Bonnie M., Clark, Robert L., Jones, Howard and Zimmerman, Morris: "Selective Inhibition of Human Leukocyte Elastase and Bovine a-Chymotrypsin by Novel Heterocycles", Journal of Biological Chemistry, No. 22, Issue of Nov. 25, pp. 11603-11606, 1981.
Dorn, Conrad P., Zimmerman, Morris, Yang, Shu Shu, Yurewicz, Edward C., Ashe, Bonnie M., Frankshun, Robert and Jones, Howard: "Proteinase Inhibitors. 1. Inhibitors of Elastase", Journal of Medicinal Chemistry, 1977, vol. 20, No. 11.
Doyle, B. B., Traub, W., Lorenzi, G. P., Brown, III, F. R. and Blout, E. R.: "Synthesis and Structural Investigation of Poly(L-alanyl-L-alanyl-glycine)", J. Mol. Biol. (1970) 51, 47 59.
Vlasak, J., Rypacek, F., Drobnik, J. and Saudek, V.: "Properties and Reactivity of Polysuccinimide" Institute of Macromolecular Chemistry, Czechoslovak Academy of Sciences, 162 06 Prague 6, Czechoslovakia.
Brown, Harold H.: "A Study of 2,4,6-Trinitrobenzenesulfonic Acid for Automated Amino Acid Chromatography".
Neri, Paolo, Antoni, Guido, Benvenuti, Franco, Cocola, Francesco and Gazzei, Guido: "Synthesis of , -Poly[(2-hydroxyethyl)-DL-aspartamide], a New Plasma Expander", Journal of Medicinal Chemistry, 1973, vol. 16, No. 8.
Tsuji, K., Agha, B. J., Shinogi, M., Digenis, G. A.: "Peptidyl Carbamate Esters: A New Class of Specific Elastase Inhibitors", Biochemical and Biophysical Research Communications, vol. 122, No. 2, 1984, Jul. 31, 1984 pp. 571-576.

*Primary Examiner*—Merrell C. Cashion, Jr.
*Assistant Examiner*—A. M. Davenport
*Attorney, Agent, or Firm*—Lowe, Price, LeBlanc & Becker

[57] ABSTRACT

Pharmaceutical compositions and methods of inhibiting the enzyme elastase and increasing the biological half-life and/or potency in terms of inhibitory activity of the enzyme elastase of peptide compounds is achieved by use of a polymer of the formula P—(L—R)$_q$ wherein P is a polymer containing at least one unit of the formula $(A_nB_n)$ wherein $A_nB_n$ is substantially nonbiodegradable, and has an average molecular weight of about 1,000 to 5,000 daltons, L is a covalent bond or a linker group and R is a peptide.

15 Claims, No Drawings

POLYMER BOUND ELASTASE INHIBITORS

This application is a continuation of application Ser. No. 07/242,294 filed Sep. 9, 1988 and now abandoned.

TECHNICAL FIELD

This invention relates to potent polymeric inhibitors of the enzyme elastase and to their utilization for inhibiting the activity of the enzyme in animals and humans. The invention also relates to a method of increasing the biological half-life and/or the elastase enzyme inhibitory activity of a peptide elastase inhibitor by binding multiple units of the inhibitor to a hydrophilic, flexible and substantially non-biodegradable polymer.

BACKGROUND ART

Proteinases from polymorphonuclear leukocytes and macrophages, especially elastases (human leukocyte elastase and cathepsin G), appear to be responsible for the chronic tissue destruction associated with inflammation, arthritis and emphysema. During infection or inflammation, the normal lung is protected from proteolytic digestion by the protease inhibitor, $\alpha_1$-antitrypsin. The protective mechanism appears to be nonoperative in individuals with an $\alpha_1$-antitrypsin deficiency due to genetic or other causes. Synthetic elastase inhibitors capable of replacing $\alpha_1$-antitrypsin may therefore be useful in the treatment of pulmonary emphysema and related diseases.

Several types of elastase inhibitors have been reported in the literature. These include peptide chloromethyl ketones as described by P. M. Tuhy and J. C. Powers, "Inhibition of Human Leukocyte Elastase by Peptide Chloromethyl Ketones", FEBS Letters, 50, 359-61 (1975); J. C. Powers, B. F. Gupton, A. D. Harley, N. Nishino and R. J. Whitley, "Specificity of Porcine Pancreatic Elastase, Human Leukocyte Elastase and Cathepsin G. Inhibition with Peptide Chloromethyl Ketones", Biochem. Biophys. Acta. 485, 156-66 (1977); azapeptides, C. P. Dorn, M. Zimmerman, S. S. Yang, E. C. Yurewicz, B. M. Ashe, R. Frankshun and H. Jones, "Proteinase Inhibitors. 1. Inhibitors of Elastase", J. med. Chem., 20, 1464-68 (1977); J. C. Powers and B. F. Gupton, "Reaction of Serine Proteases with Aza-amino Acid and Aza-peptide Derivatives", Meth. Enzymol., 46, 208-16 (1977); sulfonyl fluorides, T. Yoshimura, L. N. Barker and J. C. Powers, "Specificity and Reactivity of Human Leukocyte Elastase, Porcine Pancreatic Elastase, Human Granulocyte Cathepsin G, and Bovine Pancreatic Elastase, Human Granulocyte Cathepsin G, and Bovine pancreatic Chymotrypsin with Arylsulfonyl Fluorides. Discovery of a new series of potent and specific irreversible Elastase Inhibitors", J. Biol. Chem. 257, 5077-84 (1982); heterocyclic acylating agents, M. Zimmerman, H. Morman, D. Mulvey, H. Jones, R. Frankshum and B. M. Ashe, "Inhibition of Elastase and Other Serine Proteases by Heterocyclic Acylating Agents", J. Biol. Chem. 25, 9848-51 (1980); B. Ashe, R. L. Clark, H. Jones and M. Zimmerman, "Selective Inhibition of Human Leukocyte Elastase and Bovine $\alpha_1$-Chymotrypsin by Novel Heterocycles", J. Biol. Chem. 256: 11603-6(1981); imidazole N-carboxamides, W. C. Groutas, R. C. Badger, T. D. Ocain, D. Felder, J. Frankson and M. Theodorakis, Biochem. Biophys. Res. Commun., 95, 1890 (1980); and p-nitrophenyl-N alkyl carbamates, R. E. Scofied, R. P. Werner and F. Wold, "p-Nitrophenyl Carbamates as Active-Site-Specific Reagents for Serine Proteases", Biochemistry, 16, 2492 (1977).

Some peptide chloromethyl ketones have been shown to be effective in preventing elastase induced emphysema in animal models, A. Jaoff and R. Dearing, "Prevention of Elastase Induced Experimental Emphysema by Oral Administration of Synthetic Elastase Inhibitor", Am. J. Respir. Dis. 121, 1025-3 (1980). However, there is considerable question whether such reactive agents can be used for treating emphysema in humans. This is not surprising since the alkylating moieties in these inhibitors might render them toxic when used on a continuous basis. To be suitable for human use, an enzyme inhibitor has to show a high degree of selectivity and must have minimal toxic side effects. As a result, most drugs are molecules that reversibly bind to specific enzymes or receptor sites. Examples are the carbamate esters physostigmine and neostigmine which have been clinically used as inhibitors of acetyl choline esterases (A. G. Gilman, L. S. Goodman, and A. Gilman, "The pharmacological Basis of Therapeutics", p. 101, MacMillan Publishing Co. (1980)).

U.S. Pat. No. 4,643,991, Tsuji K. et al, B.B.R.C. 122(2):571 (1984) and Digenis, G. A. et al, J. Med. Chem. 29:1468 (1986) describe peptide elastase inhibitors which are specific and active-site directed and are not subject to the disadvantages associated with other prior art compounds for this purpose.

However, there is still a need for elastase enzyme inhibitors which are specific and active-site directed of increased biological half-life and elastase enzyme inhibitory activity.

DISCLOSURE OF THE INVENTION

This invention relates to a polymer of the formula $$P-(L-R)_q$$

wherein

P is a polymer comprising at least one unit of the formula $(A_mB_n)$, wherein $(A_mB_n)$ is substantially non-biodegradable and has an average molecular weight of about 1,000 to 500,000 daltons, m and n may be the same or different and are about 5 to 3,000, and A and B may be the same or different and at least one of A and B is capable of covalently binding to one of L and R;

R is a compound selected from the group consisting of a compound C of the formula

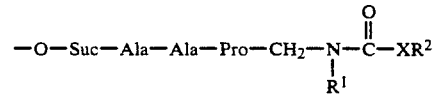

wherein X is oxygen or sulfur;

R' is selected from the group consisting of straight and secondary branch-chained $(C_1-C_4)$ alkyl, $(C_2-C_3)$ alkenyl, $(C_2-C_4)$ alkynyl, $(C_3-C_6)$ cycloalkyl, and benzyl, and $R^2$ is selected from the group consisting of substituted and unsubstituted phenyl, wherein the substituents are selected from the group consisting of nitro, and pentafluoro, benzyl, $CH_2CF_2CF_2CF_3$, 1-lower alkyl tetrazolyl, 1-phenyltetrazolyl, 2-thioxo-3-thiazolidinyl-, pyridyl and benzothiazolyl, provided that when $R^2$ is p-nitrophenyl R' is other than tert-butyl, benzyl or cyclohexyl, and when X is sulfur $R^2$ is other than benzyl;

a compound D of the following general formula:

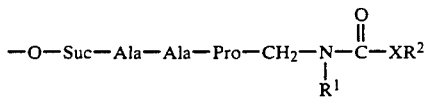

wherein

X is O or S,

R² is selected from the group consisting of phenyl, nitrophenyl, fluorophenyl, —CH₂CF₂CF₂CF₃, 1-lower alkyltetrazolyl, 1- phenyltetrazolyl, benzyl, 2-thioxo-3-thiazolidinyl, pyridyl and benzothiazolyl, and R' is selected from the group consisting of straight or secondary branch chained (C₁-C₄) alkyl, (C₂-C₃) alkenyl, (C₂-C₄) alkynyl, (C₃-C₆) cycloalkyl, and benzyl, provided that when R² is p-nitrophenyl R' is other than tertiary-butyl, benzyl or cyclohexyl, and when X is sulfur R² is other than benzyl; and a compound E of the formula

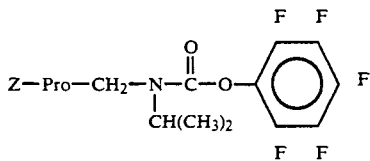

wherein

Z is -O-Suc-Ala-Ala;

each said R being covalently bound to L or to one of A and B,

L is selected from the group consisting of a covalent bond and a linker group which is covalently bound to R and one of A and B; and q is about 1 to m+n.

This invention also relates to an elastase enzyme inhibiting composition, comprising an elastase inhibiting amount of the polymer described above, and a carrier.

Also part of this invention is a method of inhibiting the enzyme elastase in an animal or human in need of such treatment comprising administering to said animal or human an elastase-inhibiting amount of the polymer of this invention.

This invention also relates to a method of inhibiting the enzyme elastase in an animal or human in need of such treatment comprising administering to said animal or human the elastase enzyme inhibiting composition of this invention described above.

Also part of this invention is a method of increasing the biological half-life of a compound selected from the group consisting of a compound C of the formula

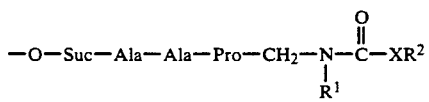

wherein

X is oxygen or sulfur;

R' is selected from the group consisting of straight and secondary branch- chained (C₁-C₄) alkyl, (C₂-C₃) alkenyl, (C₂-C₄) alkynyl, (C₃-C₆) cycloalkyl, and benzyl; and R² is selected from the group consisting of substituted and unsubstituted phenyl, wherein the substituents are selected from the group consisting of nitro, and penta-fluoro, benzyl, CH₂CF₂CF₂CF₃, 1-lower alkyl tetrazolyl, 1-phenyltetrazolyl, 2-thioxo-3-thiazolidinyl-, pyridyl and benzothiazolyl, provided that when R² is p-nitrophenyl R' is other than tert-butyl, benzyl or cyclohexyl, and when X is sulfur R² is other than benzyl;

a compound D of the following general formula:

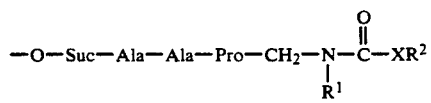

wherein

X is O or S,

R² is selected from the group consisting of phenyl, nitrophenyl, fluorophenyl, —CH₂CF₂CF₂CF₃, 1-lower alkyltetrazolyl, 1- phenyltetrazolyl, benzyl, 2-thioxo-3-thiazolidinyl, pyridyl and benzothiazolyl, and R' is selected from the group consisting of straight or secondary branch chained (C₁-C₄) alkyl, (C₂-C₃) alkenyl, (C₂-C₄) alkynyl, (C₃-C₆) cycloalkyl, and benzyl, provided that when R² is p- nitrophenyl R' is other than tertiary-butyl, benzyl or cyclohexyl, and when X is sulfur R² is other than benzyl; and a compound E of the formula

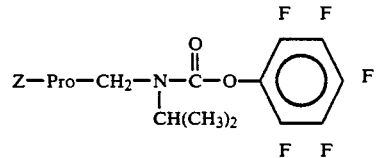

wherein

Z is -O-Suc-Ala-Ala each said R being covalently bound to L or to one of A and B, L is selected from the group consisting of a covalent bond and a linker group which is covalently bound to R and one of A and B; and q is about 1 to m+n.

In addition, this invention also relates to a method of increasing the elastase enzyme inhibitory activity of a compound selected from the group consisting of a compound C of the formula

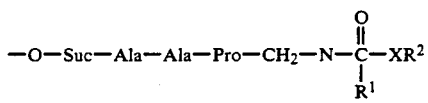

wherein

X is oxygen or sulfur,

R² is selected from the group consisting of phenyl, p-nitrophenyl, pentaflurophenyl, —O—CH₂CF₂CF₂CF₃, 1-methyltetrazolyl, 1-phenyltetrazolyl, 2-thioxo3-thiazolidinyl, pyridyl, benzyl and benzothiazolyl, and R' is selected from the group consisting of lower alkyl, lower alkenyl, lower alkynyl and benzyl, provided that when R is p- nitrophenyl R' is other than tert-butyl, and when X is sulfur R is other than benzyl;

a compound D of the following general formula:

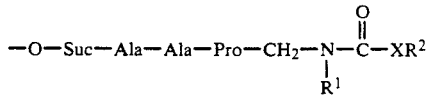

wherein

X is O or S,

R² is selected from the group consisting of phenyl, nitrophenyl, fluorophenyl, —CH₂CF₂CF₂CF₃, 1-lower alkyltetrazolyl, 1- phenyltetrazolyl, benzyl, 2-thioxo-3-thiazolidinyl, pyridyl and benzothiazolyl, and R' is selected from the group consisting of straight or secondary branch chained ($C_1$–$C_4$) alkyl, ($C_2$–$C_3$) alkenyl, ($C_2$–$C_4$) alkynyl, ($C_3$–$C_6$) cycloalkyl, and benzyl, provided that when R² is p- nitrophenyl R' is other than tertiary-butyl, benzyl or cyclohexyl, and when X is sulfur R² is other than benzyl; and a compound E of the formula

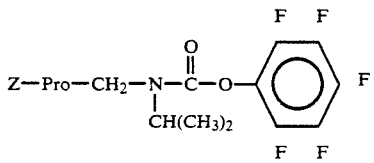

wherein

Z is MeO-Suc-Ala-Ala;

each said R being covalently bound to L or to one of A and B,

L is selected from the group consisting of a covalent bond and a linker group which is covalently bound to R and one of A and B; and q is about 5 to m+n.

A more complete appreciation of the invention and many of the attendant advantages thereof will be readily perceived as the same becomes better understood by reference to the following detailed description when considered in connection with the accompanying figures.

BRIEF DESCRIPTION OF DRAWINGS

FIG. 1 depicts the inhibition of human leukocyte elastase (HLE) by various peptidyl carbamate derivatives and α₁-proteinase inhibitor (alpha₁-PI) using MeO-Suc-Ala-Ala-Pro-VAL-NA as a substrate, where the concentration of the substrate is $1.62 \times 10^{-4}$M and the concentration of the enzyme is $3.4 \times 10^{-4}$M and FIG. 2 depicts the cumulative molecular weight distribution of the polymer-bound compound described in Example 2 (polymer IV).

FIG. 3 depicts the absorption spectrum of the polymer bound compound of Example 2 (polymer IV).

FIG. 4 shows a gel permeation chromatography (GPC) analysis of the reaction mixture of the compound and the polymer of Example 2 (compound III) at various times of the reaction.

FIG. 5 depicts the binding of the elastase inhibitory peptide to the polymer (compound III) of Example 2.

Other objects, advantages and features of the present invention will become apparent to those skilled in the art from the following discussion.

BEST MODE FOR CARRYING OUT THE INVENTION

This invention arose from a desire to improve on the biological half-life and/or potency of the elastase enzyme peptide inhibitors provided by the same inventors in U.S. Pat. No. 4,643,991. The inventors unexpectedly discovered that if multiple units of the known peptide inhibitors were covalently bound to a flexible, linear polymer the product polymers had a surprisingly high biological half-life and/or potency with respect to the inhibition of the elastase enzyme.

The polymers provided herein have the formula

P—(L—R)$_q$ wherein

P is a polymer comprising at least one unit of the formula ($A_mB_n$), wherein ($A_mB_n$) is substantially non-biodegradable and has an average molecular weight of about 1,000 to 500,000 daltons, m and n may be the same or different and are about 5 to 3,000, and A and B may be the same or different and at least one of A and B is capable of covalently binding to one of L and R;

R is a compound selected from the group consisting of a compound C of the formula

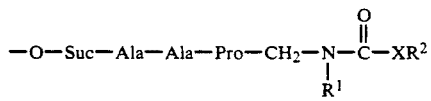

wherein

X is oxygen or sulfur;

R' is selected from the group consisting of straight and secondary branch-chained ($C_1$–$C_4$) alkyl, ($C_2$–$C_3$) alkenyl, ($C_2$–$C_4$) alkynyl, ($C_3$–$C_6$) cycloalkyl and benzyl, and R² is selected from the group consisting of substituted or unsubstituted phenyl, wherein the substituents are selected from the group consisting of nitro, pentafluoro, benzyl, CH₂CF₂CF₂CF₃, 1-lower alkyl tetrazolyl, 1-phenyltetrazolyl, 2-thioxo3-thiazolidinyl-, pyridyl and benzothiazolyl, provided that when R² is p-nitrophenyl R' is other than tert-butyl, benzyl or cyclohexyl, and when X is sulfur R² is other than benzyl;

a compound D of the following general formula

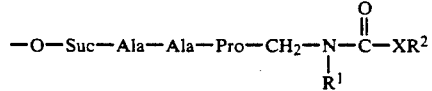

wherein

X is O or S,

R² is selected from the group consisting of phenyl, nitrophenyl, fluorophenyl, —CH₂CF₂CF₂CF₃, 1-lower alkyltetrazolyl, 1- phenyltetrazolyl, benzyl, 2-thioxo-3-thiazolidinyl, pyridyl and benzothiazolyl, and R' is selected from the group consisting of straight or secondary branch chained ($C_1$–$C_4$) alkyl, ($C_2$–$C_3$) alkenyl, ($C_2$–$C_4$) alkynyl, ($C_3$–$C_6$) cycloalkyl, and benzyl, provided that when R² is p- nitrophenyl R' is other than tertiary-butyl, benzyl or cyclohexyl, and when X is sulfur R² is other than benzyl; and a compound E of the formula

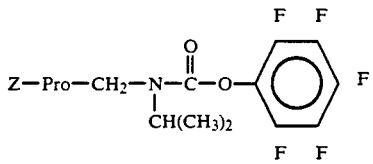

wherein

Z is MeO-Suc-Ala-Ala;

each said R being covalently bound to L or to one of A and B,

L is selected from the group consisting of a covalent bond and a linker group which is covalently bound to R and one of A and B; and q is about 1 to m+n.

These polymers are suitable for the inhibition of the activity of the elastase enzyme both in vitro and in vivo. When they are utilized for inhibiting the elastase enzyme in vivo, solely pharmaceutically-acceptable polymers are to be utilized. These are known in the art and need not be specifically referred to herein.

When the polymers of this invention are utilized in the in vitro inhibition of the enzyme they need not be pharmaceutically-acceptable. Accordingly, a significantly larger number of polymers are ultimately suitable for the design of the inhibitory polymers of this invention for use in vitro.

In general the polymers suitable for use in this invention are water soluble polymers, and preferably polymers having a flexible backbone structure which are not easily biodegradable and which consequently have a prolonged biological half life. Even more preferred are polymers which are water soluble and substantially non-biodegradable but which also have a flexible polymer backbone. A high flexibility exhibited by the polymer is helpful in increasing the accessibility of the polymer bound inhibitory molecule to the enzyme.

Suitable polymers for use in this invention are polymers containing amide bonds in the main chain. Particularly useful are derivatives of synthetic polyamino acids, examples of which include random copolymers of $\alpha, \beta$ hydroxy alkyl-D,L-aspartamide, e.g., poly $\alpha, \beta$-[N-(2-hydroxyethyl)-D,L-aspartamide] in which a fraction of 2-hydroxyethyl side-chains is replaced by said appended reactive moiety.

Other examples of suitable polymers include polysaccharide derivatives, especially derivatives of dextran, cellulose, carboxymethyl cellulose, alginic acid and hyaluronic acid or combinations thereof or combinations with other polymers. Yet another example of suitable polymers with oxygen atoms in the main polymer chain are polyether polymers, examples of which include polyethyleneglycol (polyoxirane), divinylethermaleic acid copolymer (pyran copolymer, DIVEMA), and the like.

Examples of polymers with $\alpha$-C-C- backbone suitable for use in this invention are copolymers prepared from mixtures of different types of monomers. One such group is a polymer formed by mixing one type of monomer which has reactive appended moieties and another type of monomer lacking such moieties. Particularly suitable are copolymers derived from hydrophilic vinylic and/or acrylic type monomers, examples of which include N-2-vinylpyrrolidone, 2-hydroxzypropylmethacrylamide, 2-hydroxyethyl methacrylate and other hydrophilic esters and amides of arylic and methacrylic acid which are well known in the art. Suitable monomers containing appended reactive moieties for preparation of copolymers for use in this invention include, e.g., maleic acid anhydride and reactive esters of acrylic and methacrylic acid. Particularly suitable are, e.g., glycidyl acrylate, glycidylmethacrylate, p-nitrophenyl, N-hydroxysuccinimide, pentachlorophenyl or/and pentafluorophenyl esters of methacrylic and acrylic acids, wherein the alkoxy moiety of the reactive ester can be either bound directly to the carbonyl of methacrylic or acrylic acid or it can be bound via a spacer linker. Suitable spacer linkers for use in these types of polymers are generally known in the art. Examples of particularly suitable polymers include poly(N-vinylpyrrolidone), copoly-(N-vinylpyrrolidone-co-maleic acid anhydride), copoly-(N-vinylpyrrolidone-co-methacryloyl-N-Hydroxysuccinimide, copoly(N-(2-hydroxypropyl)methacrylamide-co-methacryloyl p-Nitrophenyl ester) and other copolymers formed by the monomers indicated above.

The linkers or spacers optionally incorporated in the polymer-bound inhibitors of the invention must contain at least two reactive groups. One of the reactive groups must be capable of covalently bonding to the appended moiety present in at least some of the monomer units contained in the polymer. The other reactive group must be capable of covalently bonding to a reactive group present in the free inhibitor molecule which is not involved in the binding to the active site of the enzyme. Suitable linkers are known in the art and need not be specifically described herein. One group of linkers which has been found suitable for use with this invention is that encompassing flexible backbone hydrocarbons containing at least two reactive groups. Suitable are reactive groups such as hydroxyl, sulfhydryl, amino, carboxyl, hydrazino and hydrazido, among others. However, other groups may also be utilized. The length of the linker or spacer may vary as desired for particular applications. Typically, ($C_2$-$C_{20}$) hydrocarbon linkers are utilized, preferably linear hydrocarbons. However, other types of molecules may also be incorporated herein.

A particularly suitable type of linker has been found to be those comprising ($C_1$-$C_{20}$) hydrocarbons having covalently bonded substituents to the first and last carbon atoms such as hydroxy amines. Other examples suitable for use in this invention are $\alpha, \omega$-diamines, $\alpha, \omega$-diamino alcohols and $\alpha, \omega$-diamino acids.

The novel substituted carbamate compound polymers, the pharmaceutical compositions containing them and the method for using these polymers are exemplified in the specific inhibition of porcine pancreatic elastase and human leukocyte elastase without affecting the similar serine dependent proteases, bovine pancreatic trypsin and chymotrypsin.

It is known from the art that proteases from polymorphonuclear leukocytes and macrophages, especially elastases (human leukocyte HL elastase and cathepsin G) appear to be responsible for chronic tissue destruction associated with inflammation, arthritis and emphysema. During infection or inflammation, the normal lung is protected from proteolytic digestion by the protease inhibitor, $\alpha_1$-antitrypsin. This protective mechanism appears to be non-operative in individuals with an $\alpha_1$-antitrypsin deficiency due to genetic or other causes. Synthetic elastase inhibitors capable of replacing $\alpha_1$-antitrypsin are therefore useful in the treatment of pulmonary emphysema and related diseases.

According to the present invention, a class of known compounds containing carbamate functionality and oligopeptides which are active-site directed inhibitors of elastase in animas and humans have been found to exhibit an increased biological half-life and/or potency when multiple units thereof are bound to a substantially non-biodegradable polymer. Polymers with multiple-bound peptidyl carbamate chains therefore provide an opportunity to incorporate multiple inhibitory moieties into a single unit, thereby increasing the efficiency of the transfer of the acrylating moiety to the active site of the enzyme. This, in turn, optimizes the affinity of the polymer inhibitor towards the enzyme in comparison with the low-molecular weight inhibitory peptides themselves.

The nature of the acylating moiety can be varied to optimize the duration of enzymatic inactivation as desired.

It is theorized that the mechanism of the invention takes advantage of the fact that carbamate esters react with proteases and esterases at the carbonyl carbon by losing the alkoxy portion thereof and transferring the carbamylating moiety to the active side of the enzyme. Deacylation then leads to the recovery of enzymatic activity.

Suitable carbamate compounds which are active in accordance with the above proposals as elastase inhibitors are various. These compounds are carbamates substituted by oligopeptides and may generally be described by the following general formula C 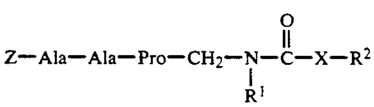 wherein Z is selected from the group consisting of R″O-Suc-, wherein R″ is $(C_1-C_3)$alkyl, $CF_3CO$— and/or a linker to a polymer.

X is oxygen or sulfur;

R′ is selected from the group consisting of straight and secondary branch-chained $(C_1-C_4)$ alkyl, $(C_2-C_3)$ alkenyl, $(C_2-C_4)$ alkynyl, $(C_3-C_6)$ cycloalkyl and benzyl, and $R^2$ is selected from the group consisting of substituted or unsubstituted phenyl, wherein the substituents are selected from the group consisting of nitro, pentafluoro, benzyl, $CH_2CF_2CF_2CF_3$, 1-lower alkyl tetrazolyl, 1-phenyltetrazolyl, 2-thioxo3-thiazolidinyl-, pyridyl and benzothiazolyl, provided that when $R^2$ is p-nitrophenyl R′ is other than tert-butyl, benzyl or cyclohexyl, and when X is sulfur $R^2$ is other than benzyl.

In more preferred embodiments, the inhibitory peptides may be described by the following general formulas D or E 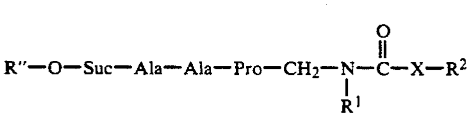 wherein R′ is $(C_1-C_3)$ alkyl or a suitable linker to the polymer, X is oxygen or sulfur, and $R^2$ is selected from the group consisting of phenyl, fluorophenyl, nitrophenyl, 1-phenyltetrazolyl, 1-lower alkyl tetrazolyl, benzyl, 3-thiazolidinyl, pyridyl and benzothiazolyl, and R′ is straight or secondary branch chained $(C_2-C_4)$ alkyl, $(C_2-C_4)$ alkenyl, and $(C_2-C_4)$ alkynyl, provided that when $R^2$ is p-nitrophenyl R′ is other than tertiary-butyl, and when X is sulfur $R^2$ is other than benzyl; and 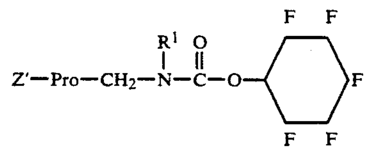 wherein Z′ is selected from the group consisting of MeO-Suc-Ala-Ala, $CF_3CO$-Ala-Ala and a suitable linker connecting this compound with a polymer; and R′ is as defined above but is preferably isopropyl.

Suitable linkers are known in the art for the particular type of atom groupings present herein.

In the inhibitory peptides suitable for use herein, the peptidyl carbamates are those wherein the amino portion contains the oligopeptide and the peptide portion is so chosen as to increase the specificity of the carbamate ester for elastase.

The peptides for the individual inhibitory compounds may be prepared by a sequential series of reactions beginning with L-proline protected on the ring nitrogen with ultimate coupling to the peptide. In the first step, an N-protected proline, e.g., N-t-Boc-L-proline, is reacted with diazomethane to obtain the diazoketone followed by treatment with HCL to obtain the chloromethyl ketone protected L-proline. The chloromethyl ketone thus obtained is reacted with the appropriate amine $H_2NR'$ to form the protected amine derivative. The amine is in turn reached with the appropriate chloroformate or thiochloroformate and deprotected by reaction with an acid such as HCl to provide the HCl salt. This compound is then coupled with Z-Ala-Ala by the mixed carbonic anhydride method to provide the compounds of the invention. The Z-Ala-Ala compounds are obtained by reaction of Ala-Ala with methyl succinic acid N-hydroxy succinimide ester when Z=R″O— Suc, e.g., MeOSuc. These Z-Aa-Ala intermediates may be prepared according to the following scheme:

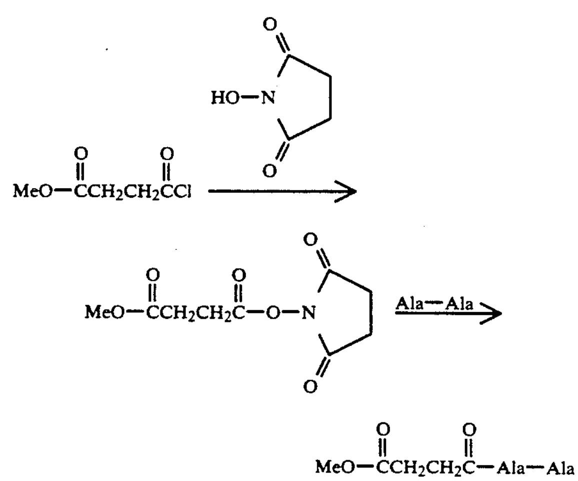

In conducting these reactions, the L-proline in the initial step is protected on the ring nitrogen by reaction with any suitable protective agent known to the art so that reaction will occur on the carboxylic acid portion of the molecule. Preferably, the nitrogen atom in the ring is protected with a known protective agent, such as t-BOC. For example, t-BOC-Pro is available commercially from Sigma Chemical Company, St. Louis, Mo. The protected proline is reacted with diazomethane by the method of Penke et al. (B. Penke, J. Czombos, L. Balaspiri, J. Peters and K. Kovacs, Helv. Chim. Acta., 53:1057 (1970)). The resulting chloromethyl ketone is then reacted with the appropriate amine. This reaction is preferably conducted in a solvent solution, such as a lower alkyl alcohol, and preferably in the presence of an alkali metal iodide. The reactants are mixed under cool temperatures and then reacted at 50° to 75° C. to complete the reaction. The evolved HCl is neutralized, as with a sodium carbonate solution, and extracted. This intermediate is then reacted with the appropriate chloroformate or thiochloroformate and deprotected with hydrogen chloride to form the carbamate portion of the molecule. This molecule is then coupled with the peptide portion of the molecule to form the final product.

This reaction procedure may be illustrated as follows:

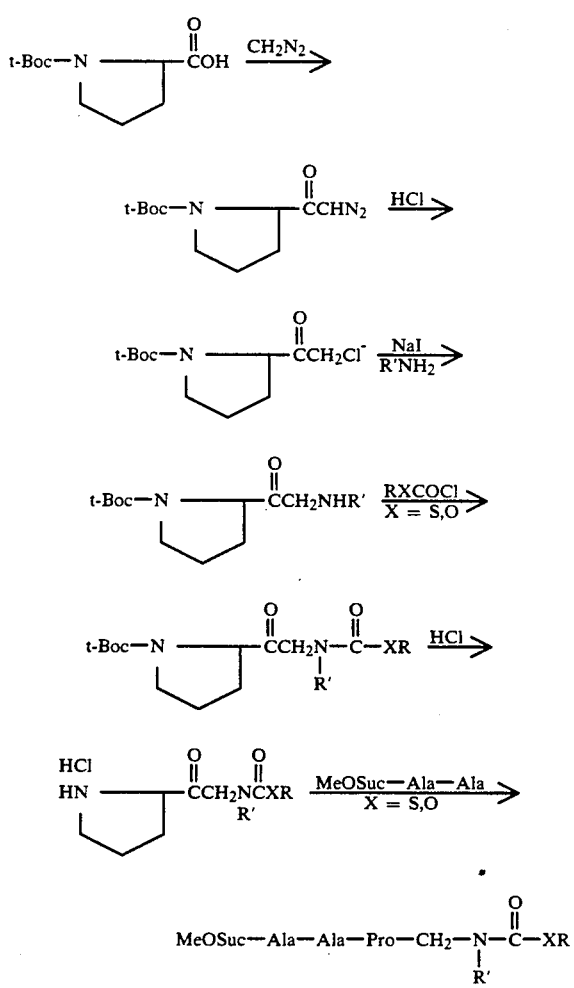

As pointed out above, the polymers of the invention may be employed as specific active site directed inhibitors of the enzyme elastase. For this purpose the polymers are preferably combined with a pharmaceutically acceptable carrier for the in vivo administration by injection or in the oral form. Conventional adjuvants and carriers may be employed in combination with about 1 to 90 wt % of the active polymer. The polymers may be administered to animals or humans at dosage amounts of about 0.1 mg/kg to 300 mg/kg, preferably about 1 mg/kg to 30 mg/kg, and still more preferably an average amount of about 12 mg/kg.

The following examples illustrate preferred embodiments of the invention but the invention is not considered to be limited thereto. In the examples and throughout this specification, parts are by weight unless otherwise indicated.

In synthesis of the compounds of the invention, melting points were determined on a Thomas-Hoover Uni-Melt apparatus and are uncorrected. 'H NMR spectra were obtained using a Varian EM-360 (60 MH$_2$) or EM-390 (90 MH$_2$) spectrometer. Infrared (IR) spectra were recorded on a Perkin-Elmer 567 spectrophotometer. Microanalyses were performed by Atlantic Microlab, Inc., Atlanta, Ga. or by Micro Analysis, Inc., Wilmington, Del.

Reactions were routinely followed by thin layer chromatography (TLC) using Whatman MK6F silica gel plates. Spots were detected by UV Spectrophotometry (254 nm), iodine or HBr-Ninhydrin spraying. Column chromatography was carried out using Silica Gel 60 (Merck, Darmstadt, Germany). All compounds were identified by spectral data and elemental analysis.

The loading of the inhibitors onto the polymers either directly or by means of a linker spacer is conducted via chemical reactions which are known in the art and need not be described here in detail. The degree of loading, i.e., density of the PC units along the polymer chain, can be varied in such a way that it is the most appropriate in accordance with the loading desired. This can be attained by varying the experimental conditions, e.g., the number of appended reactive moieties on the polymer chain, the number of spacer groups and/or the ratio of PC to the polymer in the reaction. In the Examples appended hereafter specific reaction schemes are described but are by no means intending to be limiting of the invention.

Having now generally described this invention, the same will be better understood by reference to certain specific examples which are included herein for purposes of illustration only and are not intended to be limiting of the invention or any embodiment thereof, unless so specified.

EXAMPLES

EXAMPLE 1

A peptidyl carbamate inhibitor (compound 5) suitable for the preparation of a polymer-bound inhibitor is prepared in accordance with the invention according to Scheme 1 hereinbelow.

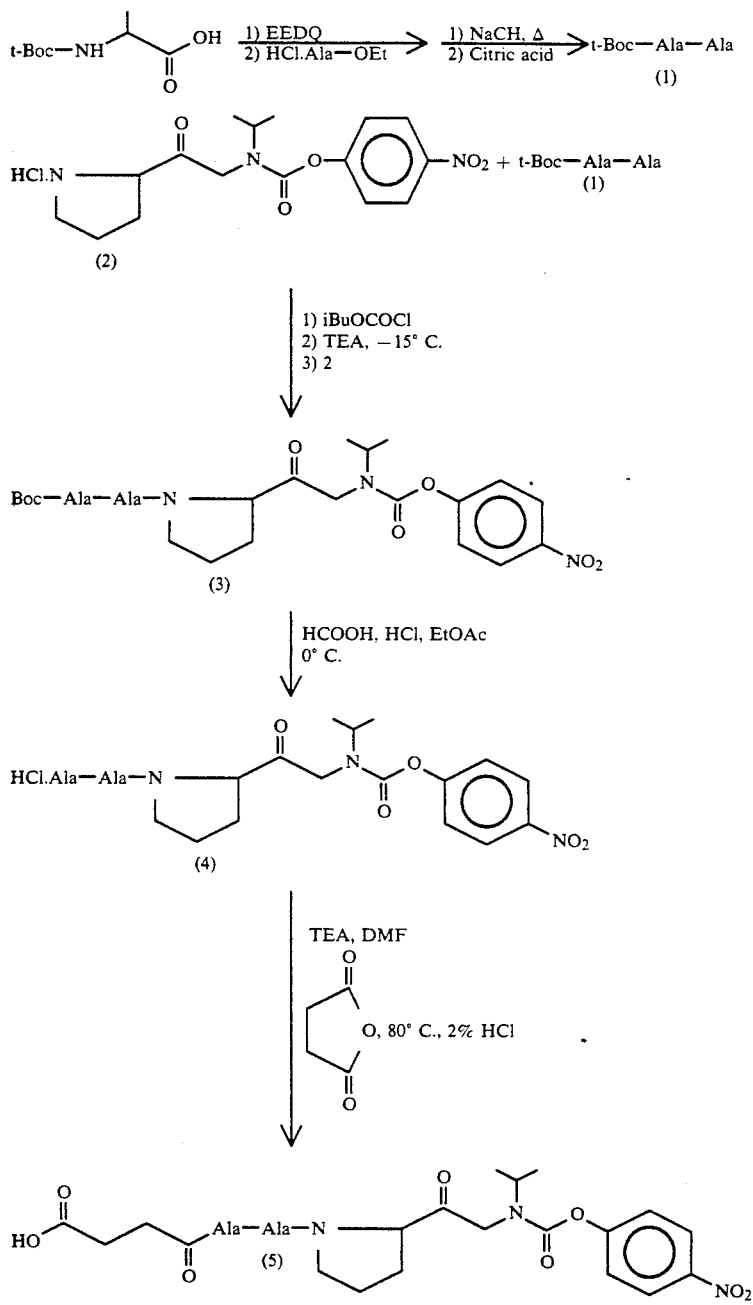

Scheme 1

The individual steps of the procedure are described hereinbelow in greater detail.

EXAMPLE 2

Synthesis of t-Boc-L-alanyl-L-alanine (Compound 1)

To a solution of t-Boc-L-alanine (5.9 g, 31.2 mmol) and L-alanine ethyl ester hydrochloride (4.8 g, 31.2 mmol) in $CH_2Cl_2/MeOH$ (4:1) is added triethyl amine (4.3 ml, 31.2 mmol) with stirring at room temperature.

To this reaction mixture is added 1-ethoxycarbonyl-2-ethoxy-1,2-dihydroquinoline (EEDQ) (8.0 g, 32.3 mmol) and stirring is continued overnight.

The mixture is then extracted into $CH_2Cl_2$ (100 mml) and washed with 10% citric acid (50 ml×3) and 5% $NaHCO_3$ (50 ml). The organic layer is dried ($Na_2SO_4$) and concentrated in vacuo.

The resulting oil is dissolved in EtOH (100 ml) and 30 ml of 1.0N KOH are added and the mixture stirred at 35–40 C. overnight. The evaporation of EtOH is followed by addition of citric acid (14 g in 50 ml $H_2$)) to neutralize the excess KOH.

The reaction mixture is then extracted into EtOAc/-tetrahydrofuran (THF) (150 ml×2 lf 1:1 mixture) and dried ($Na_2SO_4$). The solvent is then evaporated to give the product (1) which is purified by silica gel column chromatography ($CH_24Cl_2/EtOAc$ 10:1) (12.1 g, 74%) m.p. 89–91 C. in accordance with Doyle, B. B.; Traub, W.; Lorenz, G. P.; Brown, F. R.; Blout, E. R., J. Mol. Biol., 51:47 (1970).

EXAMPLE 3

Preparation of p-Nitrophenyl N-(t-Boc-L-alanyl-L-alanyl-L-prolylmethyl)-N-isopropyl carbamate (Compound 3)

To a solution of compound 1 (1.0 g, 3.9 mmol) in THF (30 ml) cooled to −30° C. is added N-methylmorpholine (0.46 mL, 4.2 mmol) and the mixture is stirred for 5 min. Isobutyl chloroformate (0.55 ml, 4.2 mmol) in THF (2 ml) is added and stirring is continued for 10 min at −15 C.

To this reaction mixture is added a suspension of compound 2 (1.3 g, 3.5 mmol) and N-methyl morpholine (0.46 ml, 4.2 mmol) in acetonitrile (40 ml) at −40 C. Stirring is continued for 1 hr at room temperature.

The reaction mixture is then filtered and the filtrate extracted with CHCl, washed with 10% citric acid (3×10 ml), dried ($Na_2SO_4$) and the solvent evaporated to give an oil.

Saturation with ethyl acetate (EtOAc) gives the solid which is purified by silica gel column chromatography (6% $CH_3OH$/CH $Cl_2$) to give compound 3 (90%).

The characteristics of compound 3 are found to be
mp:170-172 C.,
IR (K Br) $V_{max}$ 1730, 1650, 1520, 1345, 1190, 1155 $cm^{-1}$;
NMR ($CDCl_3$) δ 8.20 (2H, d, J=9 Hz), 7.20 (2H, d, J=9 Hz), 4.1-4.5 (tH, m), 3.5-3.7 (3H, m), 2.0 (4H, m), 1.5 (9H, s), 1.7-1.6 (21H, m).

EXAMPLE 4

Synthesis of p-nitrophenyl N-(L-alanyl-L-alanyl-L-proplylmethyl-N-isopropyl carbamate hydrochloride (Compound 4)

Formic acid (1.25 ml) is added to a stirring solution of a compound 3 (0.7 g, 1.02 mmol) in EtOAc (7 ml). Anhydrous HCl is then bubbled through the reaction mixture and the reaction is followed by thin layer chromatography (TLC). The solvent is evaporated and the formic acid is turned into an azeotropic mixture by addition of n-heptane. The resulting oil is used in the next step without further purification.

EXAMPLE 5

Synthesis of p-nitrophenyl N-(succinyl-L-alanyl-L-alanyl-L-prolylmethyl)-N-isopropyl carbamate (Compound 5)

To a solution of compound 4 (1.5 g, 2.9 mmol) in DMF (20 ml) are added $Et_3N$ (0.5 mL, 3.6 mmol) and succinic anhydride (0.35 g, 3.6 mmol) and the mixture is stirred at 80 C for 1.5 hr. Diethyl ether (60 ml) is then added to the cooled mixture, the precipitated $Et_3N.HCl$ is filtered and the filtrate evaporated to give a pale yellow solid. The product is then triturated with 2% HCl, filtered and recrystallized from tetrahydrofuran (THF)/ether to give 1.6 g of compound 5 (PCl) (94%).

The characteristics of compound 5 are as follows.
mp: 185-186 C.,
IR (K Br) $V_{max}$ 3300 2700, 1780, 1750, 1651, 1560, 1200 $cm^{-1}$,
NMR (DMSO $d_6$) δ 8.3 (2H, d, J=9 Hz), 1.06-1.6 (26H, m).

The anal. calculated for $C_{26}H_{35}N_9O_{10}$ ½ $H_2O$ is C, 53.43; H, 6.17; N, 11.94 and what is found is C, 53.34; H, 8.41; N, 11.93.

EXAMPLE 6

Peptidyl carbamate hemisuccinate prepared according to Example 1 (compound 5 of Scheme 1) is bound to the polymer carrier. The overall procedure is illustrated in Scheme 2 hereinbelow.

Scheme 2:
Synthesis of Polymer-bound PC Inhibitor of Example 2

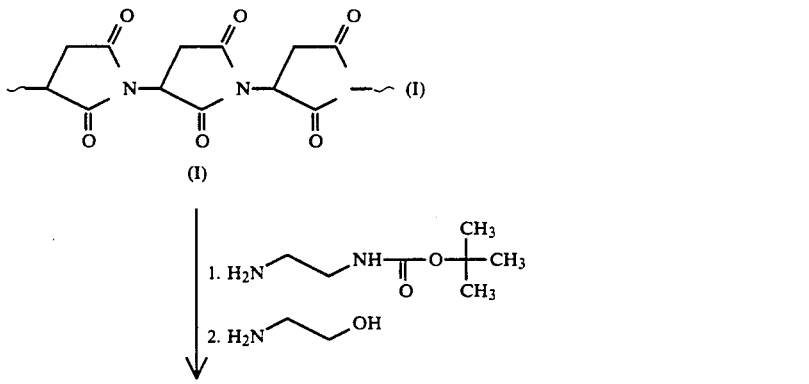

-continued
Scheme 2:
Synthesis of Polymer-bound PC Inhibitor of Example 2
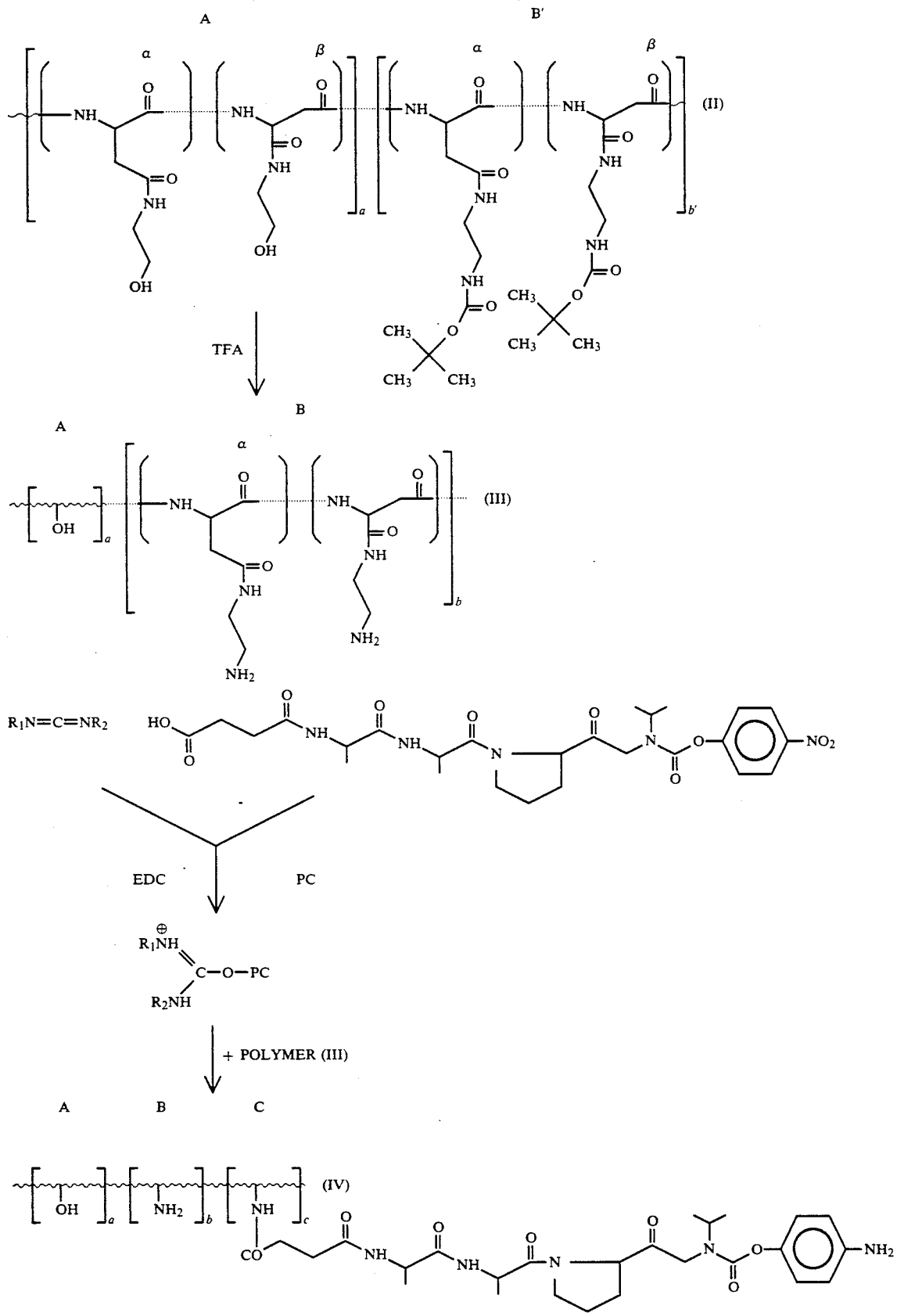

EXAMPLE 7

Synthesis of a Carrier Polymer

Polysuccinimide (I) is prepared and fractioned according to the method described by Vlasak, J., Rypacek, F., Drobnik, J., Saudek, V., J. Polymer Sci., Polymer Symp., 66:59–64 (1979).

10 g of polysuccinimide (I) (the fraction with $M_w = 32,000$) is dissolved in 50 ml of N,N'-dimethylformamide (DMF) and 2.80 g (0.01 mol) of mono-N-Boc-1,2-diaminethane benzoate, and 0.8 ml (0.01 mol) of triethylamine are added.

The reaction mixture is left at room temperature for 4 days and then 11.0 ml (0.18 mol) of 2-aminoethanol are added and the reaction is continued for another 24 hours.

The mixture is then neutralized with acetic acid, dialyzed against water and the polymer isolated by freeze-drying.

Yield: 9.20 g PHEA(AE-BOC) (compound II of Scheme 2).

PHEA(AE-BOC) (Compound II) (8.50 g) is dissolved in 30 ml of trifluoroacetic acid. The solution is left for one hour at room temperature and then dialyzed against distilled water (Visking Dialysis Tubing, Serva).

The dialyzed solution is then concentrated to a volume of 30 ml by the ultrafiltration on an Amicon YM 10 membrane and diluted again with water up to 200 ml. The ultrafiltration is repeated in the same way 5 times. The polymer is isolated from the retentate by freeze-drying.

Yield: 6.5 of PHEA(AE) (Compound III of Scheme 2).

EXAMPLE 8

Binding of Peptidylcarbamate-Hemisuccinite to the Polymer with Aminoethyl Spacer-Chains (PHEA-AE)

Peptidyl-carbamate-hemisuccinate (compound 5 of Scheme 1) (0.586 g, 0.001 mol) and N-ethyl-N'-(3-dimethylaminopropyl) carbodiimide-hydrochloride (0.23 g, 0.0012 mol) are reacted in 4.0 ml of DMF for 45 minutes in an ice bath. Then the ice cold solution containing 2.20 g of polymer III (0.0012 mol of —NH$_2$) and 0.167 ml (0.0012 mol) of triethylamine in 12 ml of DMF is added thereto and the reaction mixture is stirred at 0°–4° C. for 24 hours.

The polymer product is then dialyzed against a phosphate buffer pH 7.00 containing 0.15M NaCl. The dialyzed polymer is further purified by gel permeation chromatography (GPC) on a Sephadex G25 F column (50×300 mm) in the same buffer and the collected polymer fractions are desalted by repeated ultrafiltration and dilution on Amicon YM 10 membrane. The polymer inhibitor is isolated by freeze-drying from water.

Yield: 1.35 g PHEA(AE-PC) (Compound IV of Scheme 2).

EXAMPLE 9

Identification and Characterization of the Carrier Polymer and the Polymer-Bound Inhibitor The molecular weight distribution analysis of all polymers is performed by size-exclusion chromatography (SEC) on a mixed-bed column (Sepharose CL-4B:Sephacryl S 200 SF : : Sephadex G-25 SF, 16:5:3;13×350 mm).

0.05M phosphate buffer pH 7.50 containing 0.15M NaCl is used as eluent.

The column is calibrated with standard samples of PHEA (Rypacek, F., Saudek, V., Pytela, J., Skarda, V., Drobnik, J., Makromol. Chem. Suppl. 9:129–135 (1985)).

The elution profiles are monitored by means of an ISCO model 1840 Spectrophotometric detector. The values of molecular-weight averages, $M_w$ and $M_n$, and a cumulative molecular-weight distribution are calculated from the SEC data. These data are shown in FIG. 2.

The contents of aminoethyl side chains in polymers III and IV are determined spectrophotometrically after the reaction of aminoethyl groups with 2,3,5-trinitrobenzene sulphonic acid in accordance with Brown, H. H., Clin. Chem., 14:967, (1968). The data are shown in Table 1 hereinbelow.

TABLE 1

| Polymer Structure | Molecular Characteristics of the Polymer-Bound Inhibitor | | | | |
|---|---|---|---|---|---|
| | Composition (%) | | | Molecular weight averages | |
| | A | B | C | $M_w$ | $M_n$ |
| III | 91.2 | 8.8 | 0 | 31,600 | 21,000 |
| IV | 91.2 | 4.2 | 4.6 | 38,000 | 24,000 |

The molecular-weight-equivalent per one PC unit: 4042, i.e., 0.247 umol PC/mg of the polymer-bound PC.

The content of peptidyl carbamate units in the polymer-bound inhibitor is determined from the absorption spectrum of the polymer-inhibitor (polymer IV) assuming the value of 9700 mol$^{-1}$ l.cm for molar absorptivity of the above PC inhibitor at 276 nm (the data are shown in FIG. 3).

The time course of the binding reaction between the free PC and polymer III is followed by GPC. Typically, 10 ul samples of the reaction mixture are withdrawn at appropriate time intervals, diluted with phosphate buffer (e.g., PBS) and applied onto a Sephadex G-25 SF (11×40 mm) column. The ratio between the polymer-bound PC inhibitor and the unbound low-molecular-weight PC inhibitor is determined from the areas under the respective peaks of the elution curve monitored as the optical density at 276 nm (the absorption maximum for the free PC). The results are shown in FIG. 4 and 5.

EXAMPLE 10

Poly-$\alpha,\beta$ -(N-(2-hydroxyethyl)-D,L-aspartamide) copolymer with 6-aminohexyl spacer-chains (PHEA-AH) was prepared according to the overall procedure described in Example 2, but using mono-N-t-BOC-1,6-diaminohexane hydrochloride in place of mono-N-t-BOC-7,2-diaminoethane. 172 mg of PHEA(AH) (0.1 mmol of —NH$_2$ groups) is reacted with 58.6 mg (0.1 mmol) of peptidylcarbamate hemisuccinate prepared in Example 1 (compound 5 of Scheme 1) and 23.0 mg (0.12 mmol of N-ethyl-N'-(3-dimethylaminopropyl) carbodiimide (EDC) hydrochloride in presence of 0.12 mmol of triethylamine in dimethylformiamide (2 ml) at temperature 0°–4° C. for 20 hours. The polymer product is dialised against water and further purified by GPC on a Sephadex G-25F column (Pharmacia) and the polymer inhibitor is isolated by freeze-drying from water.

Yield: 118 mg of PHEA (AH-PC). 68% of PC originally added to the reaction is bound to the polymer producing thus polymer-bound PC containing 6.2 mole % of PC side chains.

EXAMPLE 11

The copolymer of N-2-vinylpyrrolidone and O-methacryloyl-N-oxy-succinimide (p(VP-CO-MANSu)) containing 8 mole % methacryloyl-N-oxy-succinimide comonomer is prepared by the copolymerization of said comonomers in dioxane with azo-bis-iso-butyronitril as initiator. 1.46 g p(VP-CO-MANSu) copolymer (1 mmol of N-oxy-succinimide ester groups) is reacted with 0.51 g of mono-t-BOC-1,6-diaminohexane hydrochloride (2.0 mmol) in presence of 2 mmol of triethylamine in DMF (10 ml) at temperature 50° C. for 48 hours. The polymer product is then dialysed against distiled water, the solution is then concentrated to a volume about 5 ml and 5 ml of trifluoroacetic acid is added. The reaction mixture is left at ambient temperature for 4 hours then dialysed against distilled water and the polymer is further purified by GPC on a Sephadex G-25-F column. (Sephadex: Trademark of Pharmacia Uppsala, Sweden). The polymer poly (VP-CO-MA-AH), i.e. copolymer of N-2-vinylpyrrolidone and N-(6-aminohexyl) methyacrylamide is isolated by freeze drying from aqueous solution. The mole content of aminohexyl spacer-chains is determined to be 8.9 mole % from all monomer units of the copolymer.

149 mg of poly (VP-CO-MA-AH) (0.1 mmol of —$NH_2$ groups) is reacted with 58.6 mg (0.1 mmol) of peptidyl-carbamate hemisuccinate (compound 5 of Scheme 1) obtained in Example 1 using N-ethyl-N' (3-dimethylaminopropyl) carbodiimide (EDC) hydrochloride as a coupling agent. Adopting the procedure analogous to that described in Example 2, 115 mg of the PC bound to the PVP type copolymer is obtained. The content of PC inhibitory moieties in the resulting polymer-inhibitor is determined to be 4.8 mole % from all monomer units of the copolymer.

EXAMPLE 12

1.62 g of dextran (MW 70,000; Pharmacia Uppsala, Sweden) is dissolved in 40 ml of 0.1 mol $1^{-1}$ borate buffer pH 8.00, 1.08 g of 1,2-epoxy-3-bromopropane is added and the mixture is vigorously stirred at 30° C. for 4 hours. The reaction mixture is then extracted with ethylacetate, the aqueous layer is separated, 20 ml of concentrated ammonium hydroxide is added to it and the solution is stirred at ambient temperature for 24 hours. The solution is then neutralized, dialysed against distilled water and the resulting dextran derivative (Dextran-$NH_2$) is finally purified by GPC on a Sephadex G-25 column.

Yield 0.84 g. Analysis shows 6.2 mole % of $NH_2$ groups per mole of anhydroglucose units.

58.6 mg (0.1 nmol) of peptidyl-carbamate hemisuccinate inhibitor (compound 5 of Scheme 1) prepared according to Example 1 is reacted with 21 mg of EDC (0.11 mmol) in 1.0 ml of DMF at O° C. After 60 minutes a solution of 260 mg of the above Dextran-$HN_2$ in 2 ml of 0.1 mol $1^{-1}$ borate buffer pH 9.00 is added and the mixture is stirred in an ice bath for another 16 hours. The reaction mixture is then diluted with 3 ml of 0.3 mol $1^{-1}$ NaCl and applied onto a Sephadex G-25 column. The dextran-bound PC inhibitor is isolated from the collected high-molecular-weight fraction by freeze-drying.

Yield: 210 mg, 3.2 mole % of PC inhibitory units per mole of anlydroglucose units. The inhibition of the elastase activity by the polymer-bound inhibitors prepared in accordance with the invention is evaluated according to the procedure described in detail hereinbelow.

EXAMPLE 13

Enzyme Activity Inhibition Test

All enzyme assays are performed spectrophotometrically at 25 C using CARY 219 or 2200 Varian Spectrometers. The activity of PPE is measured using 5-Boc-L-alinine p-nitrophenyl ester (Boc-Ala-ONP), as the substrate and monitoring the absorbance at 347.5 nm (p-nitrophenol). The activity of HLE is measured using methoxy succinyl-L-analyl-L-alanyl L-prolyl-L-valine p-nitroanilide (MeO-Suc-Ala-Ala-Pro-Val-NA), as the substrate and following the absorbance at 410 nm (p-nitroaniline). Active inhibitors are tested against other serine dependent proteolytic enzymes such as trypsin and chymotrypsin using their respective substrates, N-benzoyl-L-arginine ethyl ester, N-benzoyl-L-tyrosine ethyl ester and monitoring the absorbance at 253 and 256 respectively.

Screening Test (Time Course) Assays for PPE and HLE

Buffer:
  for PPE 0.05 M sodium dihydrogen phosphate buffer, pH 6.5,
  for HLE 0.1M HEPES (N-2 hydroxy ethyl piperazine-N-2-ethanesulfonic acid) buffer pH 7.4 containing 0.5M sodium chloride and 10% dimethyl sulfoxide.
Substrate:
  for PPE, t-Boc-Ala-ONP ($1.0 \times 10^{-2}$M in methanol),
  for HLE, MeO Suc-Ala-Ala-Pro-Val-NA ($1.0 \times 10^{-2}$M in dimethyl sulfoxide).
Inhibitor: $2.0 \times 10^{-3}$M in dimethyl sulfoxide
Enzyme:
  for PPE: 1.5 mg in 5 ml of 0.05M sodium phosphate buffer, pH 6.5.
  for HLE: 1 mg in 2.4 ml of 0.05M sodium acetate buffer, pH 5.5.
Procedure:
  0.1 ml of the inhibitor and 0.1 ml of the substrate are added to 2.7 ml of sodium phosphate buffer in two quartz cuvettes The cuvettes are thermally equilibrated in the spectrophotometer for two minutes and the absorbance balanced at 347.5 nm.
  PPE (0.1 ml in buffer) is added to the sample cuvette, and 0.1 ml buffer is added to the reference cuvette. The mixture is shaken for twenty seconds and the increase in absorbance monitored for thirty minutes.

Control Experiment 0.1 ml dimethyl sulfoxide are added to both cuvettes instead of inhibitor solution.

Methods of Enzymatic Assay

EXAMPLE 14

Steady State Kinetics for Determination of $K_j$ of Polymer-Bound PC Inhibitor and Free PC Inhibitor Reagents:
Buffer: 0.1M HEPES (N-2 hydroxy ethyl piperazine-N-2-ethanesulfonic acid) buffer pH 7.5 containing 0.05M NaCl and 10% dimethyl sulfoxide.
Substrate: MeO-Suc-Ala-Ala-Pro-Val-NA, (1.27, 8.47, 4.23)$\times 10^{-3}$M in dimethyl sulfoxide.
Enzyme: for HLE: 0.27 mg in 4.2 ml of 0.05M sodium acetate buffer, pH 5.5.

Inhibitor: Polymer-bound inhibitor (2.09, 1.05, 0.42, 0.21)×10$^{-5}$M in 0.05M potassium dihydrogen phosphate buffer, pH 6.5.

Free inhibitor (6.98, 3.49, 1.74, 0.70)×10$^{-3}$M in dimethyl sulfoxide.

Procedure: 33 ul of substrate, 33 ul of inhibitor and 33 ul of dimethylsulfoxide (or 33 ul of HEPES buffer for the free PC inhibitor experiments) are added to 1.9 ml of HEPES buffer in each of two quartz cuvettes. The curvettes are thermally equilibrated in the spectrophotometer at 25 C for two minutes, and the absorbance is balanced at 410 nm.

The enzyme (33 ul) is added to the sample cuvette and 0.05M sodium acetate buffer (33 ul) added to the reference cuvette. After shaking the mixture for fifteen seconds, the increase in absorbance is monitored for three minutes at 410 nm.

Controls:

Controls are run by adding 33 ul of 0.05M potassium dihydrogen phosphate buffer pH 6.5 in place of polymer-bound PC inhibitor (04 33 uL of dimethylsulfoxide in place of free PC inhibitor).

The Ki values are determined from Dixon plots and slope replots of Lineweaver-Burke plots. The Ki for polymer bound free PC inhibitor is 8.0×10$^{-7}$M and the Ki for the free PC inhibitor is 0.4–1.0×10$^{-5}$M.

EXAMPLE 15

Preincubation Method (Percent Enzymatic Activity Remaining) (for Ki Determination)

Regents:

Buffer: 0.1M Hepes buffer pH 7.5 containing 0.05M sodium chloride and 10% dimethyl sulfoxide, Substrate: MeO-Suc-Ala-Ala-Pro-Val-NA, 1.26×10$^{-2}$M in dimethyl sulfoxide.

Inhibitor: Polymer bound free PC inhibitor (4.56, 1.82, 0.91, 0.45)×10$^{-5}$M in 0.1M Hepes buffer pH 7.5 containing 0.05M NaCl and 10% dimethyl sulfoxide.

Enzyme: 2.1×10$^{-6}$M in 0.05M sodium acetate buffer pH 5.5.

Procedure: 33 ul of the inhibitor and 33 ul of the enzyme are added to 1.9 ml of the 0.1M Hepes buffer in a quartz cuvette and mixed. The reference cuvette contains 33 uL of the inhibitor, 33 u of 0.05M sodium acetate buffer and 1.90 ml of 0.1M Hepes buffer The cuvettes are thermally equilibrated in a spectrophotometer for 2 minutes and the absorbance balanced at 410 nm. At the end of a predetermined incubation period (2.5 to 20 minutes), 33 ul of substrate is added to both the reference and sample cuvettes and the mixtures are shaken for 15 seconds. The reaction is then monitored for 3 minutes and the release of p-niroaniline recorded at 410 nm.

Control:

Control is conducted as above, except that 33 ul of 0.1M Hepes buffer is used instead of inhibitor, and is considered as 100% activity.

Ki values are obtained from a reciprocal plot of $k_{obs}$ (pseudo first-order rate constant for inhibition) vs. inhibitor concentration.

EXAMPLE 16

Determination of Presence or Absence of Tight Binding for Polymer-bound free PC Inhibitor Reagents Buffer: 0.1M Hepes buffer containing 0.05M NaCl and 20% dimethyl sulfoxide pH 7.5.

Substrate: MeO-Suc-Ala-Ala-Pro-Val-NA, 4.23×10$^{-3}$M in dimethyl sulfoxide.

Inhibitor: Polymer bound or free pC inhibitor (5.58, 2.79, 2.15, 1.86, 1.40, 0.933, 0.698, 0.349, 0.209, 0.105)×10$^{-4}$M in 0.1M Hepes buffer containing 0.05M NaCl and 10% dimethyl sulfoxide pH 7.5.

Enzyme: 2.25×10$^{-6}$M in 0.5M sodium acetate buffer pH 5.5.

Procedure: 33 ul of the substrate and 33 ul of the inhibitor are added to 1.9 ml of the 0.1M Hepes buffer in each of two quartz cuvettes, thermally equilibrated for 2 minutes at 25° C., and absorbance balanced at 410 nm. The enzyme (33 ul) is added to the sample cuvette and the mixture shaken for 15 seconds The release of p-nitroaniline is followed at 410 nm for 3 minutes. 0.05M sodium acetate buffer (33 ul) is added to the reference cuvette in place of the enzyme.

Control experiment:

Conducted as above, but 33 ul of the 0.1M Hepes buffer is added in place of the inhibitor.

A velocity versus inhibitor concentration plot is used to demonstrate the presence of tight binding between polymer bound PCl and the enzyme.

The data obtained according to the above procedures show that the elastase inhibitory capacity (EIC) of the free peptidyl carbamate inhibitor is not only retained, but improved upon its binding to a water-soluble polymer.

The dissociation constant of the enzyme-inhibitor complex ($K_i$) can be used as an index of inhibitory potency. When this is done, it is found that upon binding the PC inhibitor to the polymer an at least 700 fold decrease in the $K_i$ value is observed indicating improved potency. FIG. 1 provides comparison of the inhibitory activity of the free PC inhibitor (PC-1) polymer-bound-PC inhibitor (PHEA-(AE)-PC) (P-PC11) and a natural inhibitor of elastase, i e alpha-1-proteinase inhibitor ($\alpha_1$-PI). Even if the polymer-bound PC inhibitor contains such a low content of PC units as 1.6 mole % in this case it is at least as active as $\alpha_1$-PI.

The polymer PHEA has been shown to lack toxicity (Neri, P.; Antoni, G.; Benvenute, F ; Cocola, F. and Gazzei, G., J. Med. Chem., 16:893–897 (1973). In fact, it is not possible to determine its LD$_{50}$ in mice and rats owing to its extreme tolerability over a period of 40 days. Daily i.v. injections of PHEA at doses 10 fold greater than those likely to be used in man do not induce any significant changes in total weight gain or organ weight. Moreover, no adverse effect of PHEA on the biosynthetic mechanism of the serum proteins or of blood cells has been observed (Neri et al, supra).

Additionally, PHEA has been shown to lack antigenecity. When pHEA is injected in rabbits and guinea pigs according to a wide number of immunization patterns no evidence of an immune response to it is found. (Neri et al, supra).

The invention now being fully described, it will be apparent to one of ordinary skill in the art that many changes and modifications can be made thereto without departing from the spirit or scope of the invention as set forth herein.

We claim:

1. A polymer of the formula

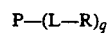

wherein

P is a water soluble polymer comprising at least one unit of the formula $(A_mB_n)$, wherein $(A_mB_n)$ is substantially non-biodegradable and has an average molecular weight of about 1,000 to 500,000 daltons, m and n may be the same or different and are about 5 to 3,000, and A and B may be the same or different and at least one of A and B is capable of covalently binding to one of L and R;

R is a compound selected from the group consisting of a compound C of the formula $$-O-Suc-Ala-Ala-Pro-CH_2-\underset{R'}{N}-\overset{O}{\underset{\|}{C}}-XR^2$$

wherein

X is oxygen or sulfur;

R' is selected from the group consisting of straight and secondary branch-chained ($C_1$–$C_4$) alkyl, ($C_2$–$C_3$) alkenyl, ($C_2$–$C_4$) alkynyl, ($C_3$–$C_6$) cycloalkyl, and benzyl, and $R^2$ is selected from the group consisting of substituted and unsubstituted phenyl, wherein the substituents are selected from the group consisting of nitro, pentafluoro, benzyl, $CH_2CF_2CF_2CF_3$, 1-lower alkyl tetrazolyl, 1-phenyltetrazolyl, 2-thioxo-3-thiazolidinyl-, pyridyl and benzothiazolyl, provided that when $R^2$ is p-nitrophenyl, R' is other than tert-butyl, benzyl or cyclohexyl, and when X is sulfur, $R^2$ is other than benzyl;

a compound D of the formula:

$$-O-Suc-Ala-Ala-Pro-CH_2-\underset{R'}{N}-\overset{O}{\underset{\|}{C}}-XR^2$$

wherein

X is O or S, $R^2$ is selected from the group consisting of phenyl, nitrophenyl, fluorophenyl, $-CH_2CF_2CF_2CF_3$, 1-lower alkyltetrazolyl, 1-phenyltetrazolyl, benzyl, 2-thioxo-3-thiazolidinyl, pyridyl and benzothiazolyl, and R' is selected from the group consisting of straight or secondary branch chained ($C_1$–$C_4$) alkyl, ($C_2$–$C_3$) alkenyl, ($C_2$–$C_4$) alkynyl, ($C_3$–$C_6$) cycloalkyl, and benzyl, provided that when $R^2$ is p-nitrophenyl R' is other than tertiary-butyl, benzyl or cyclohexyl, and when X is sulfur, $R^2$ is other than benzyl; and a compound E of the formula $$Z-Pro-CH_2-\underset{CH(CH_3)_2}{N}-\overset{O}{\underset{\|}{C}}-O-\underset{F\;\;F}{\overset{F\;\;F}{\bigcirc}}-F$$

wherein

Z is -O-Suc-Ala-Ala;

each said R being covalently bound to L or to one of A and B,

L is selected from the group consisting of a covalent bond and a linker group which is covalently bound to R and one of A and B; and q is about 1 to m+n, the resulting polymer p containing at least multiple units of R.

2. The polymer of claim 1, wherein

A is a compound of the formula $$-HN-\underset{\underset{\underset{R}{|}}{\underset{CO}{|}}}{\underset{(CH_2)_n}{\underset{|}{CH}}}-(CH_2)_m-CO- \qquad (1)$$

wherein m=o or 1 and n=b 1 or 0 respectively and R is selected from the group consisting of OH, 2-hydroxyethyl amine, 2-hydroxypropylamine, 3-hydroxypropyl amine, 2,3-dihydroxypropyl amine, 2-hydroxybutylamine and 4-hydroxybutylamine; and B is a compound of the formula (1) above, wherein R is selected from the group consisting of $NH_2$, $NH-NH_2$, $-NH-R'-NH_2$ wherein R' is ($C_2$–$C_{10}$) alkyl or ($C_6$–$C_8$) aryl, and $NH-R''-OH$ wherein R' is ($C_2$–$C_8$) alkyl or aryl.

3. The polymer of claim 1, wherein the polymer P is poly-$\alpha_1\beta$-(N(2-hydroxyethyl)-D,L-asparagine).

4. The polymer of claim 1 wherein

A is selected from the group consisting of N-2-vinylpyrrolidone, N-hydroxypropylmethacrylamide, 2-hydroxyethyl methacrylate and acrylamide, B is selected from the group consisting of amino ($C_2$–$C_6$) alkylmethacrylamide, amino ($C_2$–$C_6$) alkylacrylamide, amino ($C_2$–$C_6$) alkyl maleic acid monoamide, O-alkyl acrylate and methacrylate where alkyl is of the general formula $CH_2-CH(OH)-CH_2-NH-R'-NH_2$ where R' is $C_2$–$C_6$ hydrocarbon.

5. The polymer of claim 1, wherein the polymer P is a copolymer of poly (N-2-vinylpyrrolidone).

6. The polymer of claim 1, wherein the polymer P is a polysaccharide selected from the group consisting of dextran, carboxymethyl cellulose, alginic acid and hyaluronic acid.

7. The polymer of claim 1, wherein A and B are one and the same.

8. The polymer of claim 1, wherein L is of the formula $-NH-R-NH-$, wherein R is selected from the group consisting of a covalent bond, ($C_1$–$C_6$) alkyl, ($C_3$–$C_6$) hydroxyalkyl and ($C_6$–$C_8$) aryl, or wherein 2 to 4 of the alkyl groups are linked together by heteroatoms selected from the group consisting of N,O and S or by $-NH-CO-$.

9. The polymer of claim 1, wherein L is a covalent bond.

10. The polymer of claim 1, wherein

R is compound C;

R' is $-CH(CH_3)_2$; and $R^2$ is 1-methyltetrazol.

11. The polymer of claim 1, wherein

R is compound C; and

R' is selected from the group consisting of $-CH(CH_3)_2$, $-CH_2CH_2CH_3$, $-CH_3$, $-C(CH_3)_3$, cycopropyl, cyclohexyl and benzyl.

12. The polymer of claim 1, wherein
R is compound C; and
R² is selected from the group consisting of p-nitrophenyl, phenyl, perfluorophenyl, —OCH₂CF₂CF₂CF₃, 1-lower alkyltetrazolyl, 1-phenyltetrazolyl, pyridyl, 2-thioxo-3-thiazolidinyl and benzothiazolyl.

13. The polymer of claim 1, wherein
R is compound D;
R² is p-nitrophenyl; and
R' is isopropyl.

14. The polymer of claim 1, wherein
R is compound D;
R² is 1-methyltetrazolyl; and
R' is isopropyl.

15. The polymer of claim 1, wherein
R is compound D and is selected from the group consisting of
p-nitrophenyl N-(methyl succinyl-L-alanyl-L-alanyl-L-prolylmethyl)-N-isopropyl carbamate;
phenyl N-(methyl succinyl-L-alanyl-L-alanyl-L-prolyl methyl)-N-isopropyl carbamate;
pentafluorophenyl N-(methylsuccinyl-L-alanyl-L-alanyl-L-prolymethyl)-N-isopropyl-carbamate;
heptafluorobutyl N-(methyl succiny-L-alanyl-L-anyl-L-prolylmethyl) N-isopropylcarbamate;
1-methyl-5-tetrazolyl N-(methyl succinyl-L-alanyl-L-alanyl-L-prolylmethyl)-N-isopropylthiolcarbamate;
p-nitrophenyl N-(methyl succinyl-L-alanyl-L-alanyl-L-prolylmethyl) N-propylcarbamate;
p-nitrophenyl N-(methy succinyl-L-aanyl-L-alanyl-L-prolylmethyl)-N-cyclopropylcarbamate;
p-nitrophenyl-N-(methy succinyl-L-alanyl-L-alanyl-L-prolylmethyl)-N-methyl-carbamate;
pentafluorophenyl N-(trifluoroacetyl-L-alanyl-L-alanyl-L-prolylmethyl)-N-isopropylcarbamate;
1-methyl-5-tetrazolyl N-(methyl succinyl-L-alanyl-L-alanyl-L-prolylmethyl)-N-cyclopropylthiocarbamate;
1-methyl-5-tetrazolyl N-(methyl succinyl-L-alanyl-L-alanyl-L-prolylmethyl)-N-propylthiocarbamate;
1-methyl-5-tetrazolyl N-(methyl succinyl-L-alanyl-L-alanyl-L-propylmethyl)-N-butylthiocarbamate;
1-phenyl-5-tetrazolyl N-(methyl succinyl-L-alanyl-L-prolylmethyl)-N-isopropylthioilcarbamate; and
1-methyl-5-tetrazolyl N-(methyl succinyl-L-alanyl-L-alanyl-L-prolylmethyl)-N-allylthiolcarbamate.

* * * * *